(12) United States Patent
Harris

(10) Patent No.: US 10,633,631 B1
(45) Date of Patent: Apr. 28, 2020

(54) PLATELET RICH PLASMA PREPARATION SYSTEM AND DEVICES

(71) Applicant: Gerald R. Harris, Fort Worth, TX (US)

(72) Inventor: Gerald R. Harris, Fort Worth, TX (US)

( * ) Notice: Subject to any disclaimer, the term of this patent is extended or adjusted under 35 U.S.C. 154(b) by 446 days.

(21) Appl. No.: 15/446,201

(22) Filed: Mar. 1, 2017

(51) Int. Cl.
*C12N 5/078* (2010.01)
*B01L 3/00* (2006.01)

(52) U.S. Cl.
CPC .......... *C12N 5/0644* (2013.01); *B01L 3/5021* (2013.01); *B01L 2200/026* (2013.01); *B01L 2200/0684* (2013.01); *B01L 2200/0689* (2013.01); *B01L 2300/0832* (2013.01); *B01L 2300/0858* (2013.01)

(58) Field of Classification Search
CPC ....... B01L 2400/0478; B01L 2300/046; B01L 3/0217; B01L 3/5021; B01L 2300/0832; B01L 2200/026; B01L 2200/0684; B01L 2300/0858; B01L 2200/0689; G01N 33/491; G01N 1/40; A61M 1/3693; A61M 2005/3121; A61B 5/15003; A61B 5/150236; A61B 5/150244; B01D 21/262; B01D 2221/10; B01D 2313/08; B04B 5/0407; C12N 5/0644

See application file for complete search history.

(56) References Cited

U.S. PATENT DOCUMENTS

| 4,269,718 | A | | 5/1981 | Persidsky | |
|---|---|---|---|---|---|
| 5,762,798 | A | | 6/1998 | Bushman | |
| 5,817,279 | A | * | 10/1998 | Eilers | ...................... B01D 63/04 422/46 |
| 8,246,552 | B2 | | 8/2012 | Minassians | |
| 2002/0057996 | A1 | | 1/2002 | Bass | |
| 2011/0124106 | A1 | | 5/2011 | Froman et al. | |
| 2014/0356446 | A1 | | 12/2014 | Leach et al. | |
| 2015/0367064 | A1 | * | 12/2015 | Pennie | ................ B01L 3/50215 494/37 |

\* cited by examiner

*Primary Examiner* — Sally A Merkling
(74) *Attorney, Agent, or Firm* — Edward M. Livingston; Bryan L. Loeffler; Livington Loeffer, P.A.

(57) ABSTRACT

A platelet rich plasma preparation system and devices having a whole blood centrifuge tube (100) and a plasma centrifuge tube (200) wherein fill tubes (206) and vent tubes (113) are in fixed position and guards are provided to protect the fill tubes and vent tubes during use with a centrifuge. The fixed tubes and guards (114, 210) prevent kinks in the tubes and/or blockages that render the components of the system and the samples contained therein useless.

12 Claims, 2 Drawing Sheets

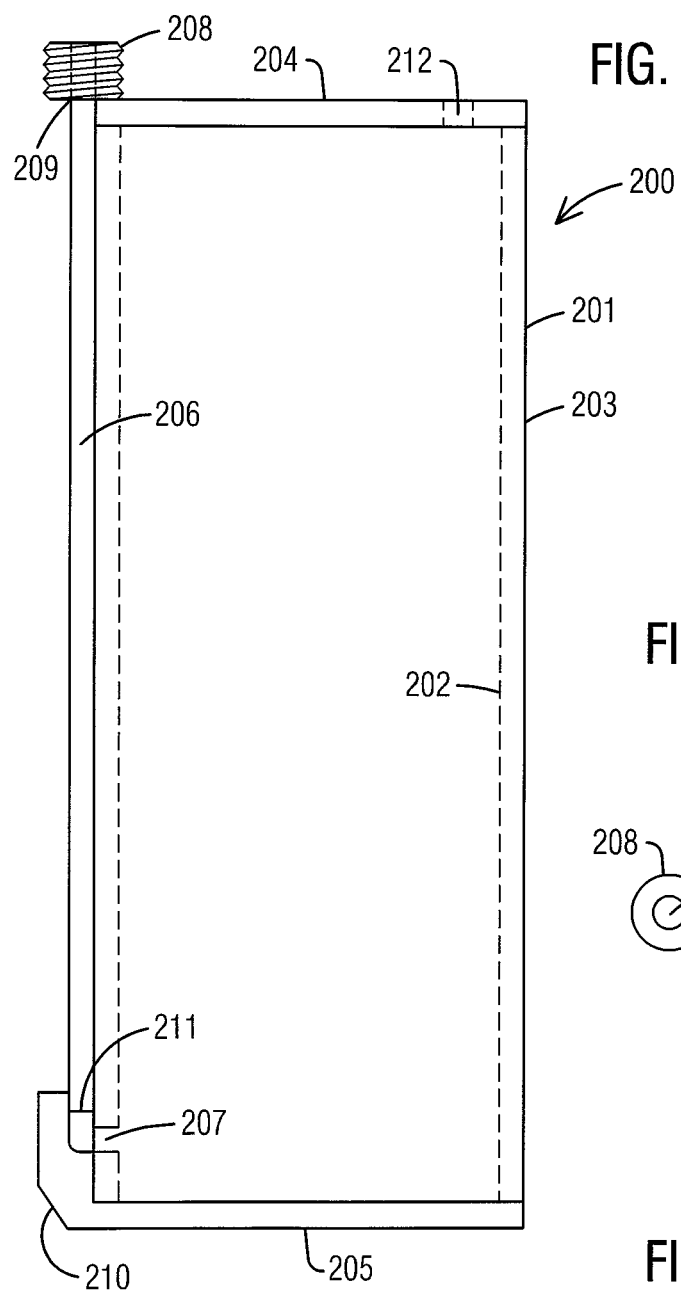
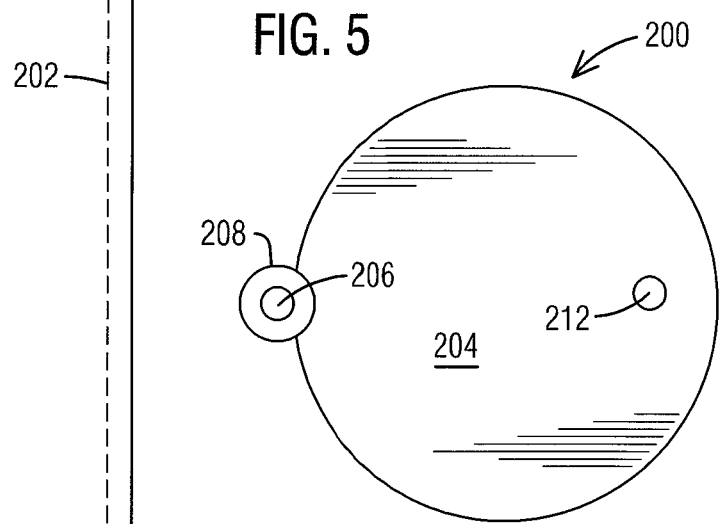
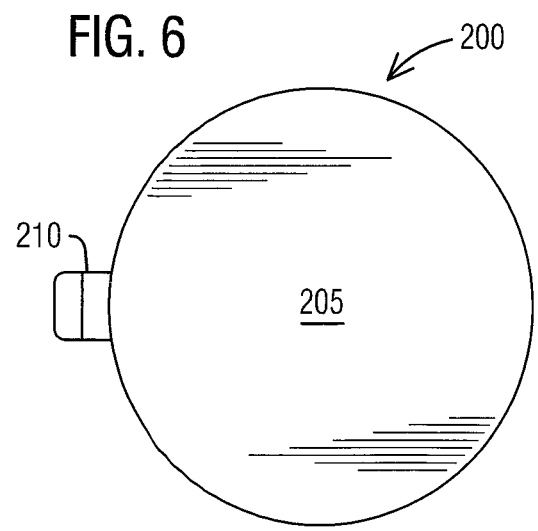

PLATELET RICH PLASMA PREPARATION SYSTEM AND DEVICES

FIELD OF THE INVENTION

The present invention relates to a system for preparing platelet rich plasma from whole blood.

BACKGROUND OF THE INVENTION

Platelet rich plasma is a biologic isolated from whole blood that is preferentially enriched for platelets. The high concentration of platelets may help improve inflammatory response, infection control, promotion of angiogenesis and tissue regeneration.

Conventional devices exist for use in separating whole blood and creating platelet rich plasma. However, many of these devices contain moving parts and/or tubes that have a tendency of becoming kinked and/or blocked, thereby rendering the devices and the samples contained therein useless.

Therefore, a need exists for platelet rich plasma preparation system that reduces the likelihood of blockages within the components of the system.

SUMMARY OF THE INVENTION

The primary object of the present invention is to provide a platelet rich plasma preparation system that reduces the likelihood of blockages within the components of the system.

The present invention fulfills the above and other objects by providing a platelet rich plasma preparation system having a whole blood centrifuge tube and a plasma centrifuge tube wherein fill tubes and vent tubes are fixed and guards are provided to protect the fill tubes and vent tubes during use with a centrifuge.

The whole blood centrifuge tube has a tubular-shaped side wall having a sealed top end panel and sealed bottom end panel. A threaded lure lock fitting is preferably located centrally on an outer surface of the top end panel in communication with an aperture located thereon. An inner surface of the whole blood centrifuge tube is angled from an outer perimeter of the aperture downward a predetermined distance on the tubular-shaped side wall, thereby creating a conical-shaped interior surface below the top panel. A piston, which is preferably a circular-shaped disk, is located within the whole blood centrifuge tube in a perpendicular position in relation to the tubular-shaped side wall. A flange is preferably located on an outer edge of the piston to create a fluid tight seal between the piston and the side wall to prevent fluid from passing by.

A vent hole is located proximate to the bottom end panel to allow communication from the interior of the whole blood centrifuge tube to a vent tube. The vent tube is preferably located on the exterior surface of the whole blood centrifuge tube and extends from the vent hole to the top end panel. A guard is preferably located proximate to the vent hole and base of the vent tube to protect both from damage and to provide a guide for inserting the whole blood centrifuge tube into a centrifuge bucket.

The plasma centrifuge tube has a tubular-shaped side wall having a sealed top end panel and sealed bottom end panel. A fill tube is preferably located on the exterior surface of the plasma centrifuge tube and extends from the vent hole to the top end panel.

A vent hole is located on the tubular-shaped side wall and preferably spaced a predetermined distance from the bottom end panel to allow retention of an amount of plasma in the bottom of the plasma centrifuge tube. A threaded lure lock fitting is preferably located a top end of the fill tube.

A guard is preferably located on a bottom end of the fill tube to protect both from damaged and to provide a guide for inserting the plasma centrifuge tube into a centrifuge bucket. A vent opening is preferably located on the top end panel to pressure within the plasma centrifuge tube to be equalized as plasma is injected into and aspirated out of the plasma centrifuge tube.

To use the whole blood centrifuge tube, a blood filled syringe is secured to the whole blood centrifuge tube via the threaded lure lock fitting, or equivalent attachment means. Then, the blood is injected into the whole blood centrifuge tube. As the blood enters the whole blood centrifuge tube, the piston is pushed downward from the top end panel and air is pushed out of the whole blood centrifuge tube out of the vent hole and vent tube. Next, the blood filled whole blood centrifuge tube is placed into a centrifuge for a desired amount of time to separate the blood into a cellular layer located on the bottom of the whole blood centrifuge tube and a plasma layer on the top of the whole blood centrifuge tube. A clean syringe is then secured to the whole blood centrifuge tube via the threaded lure lock fitting and the top layer of plasma is suctioned out of the whole blood centrifuge tube, thereby leaving the cellular layer in the whole blood centrifuge tube. As the top layer of plasma is suctioned out of the whole blood centrifuge tube, the piston is pulled upward and the air pressure underneath the piston is equalized through the vent hole and vent tube.

The plasma filled syringe is then secured to the plasma centrifuge tube via the threaded lure lock fitting, or equivalent attachment means. Then, the plasma is injected into the plasma centrifuge tube through the fill tube. Next, the plasma filled plasma centrifuge tube is placed into a centrifuge for a desired amount of time to separate platelets from the plasma to form a layer of platelets on the bottom of the plasma centrifuge tube. The plasma is then aspirated out of the plasma centrifuge tube to a level even with the fill hole, thereby leaving the layer of platelets and a small layer of plasma covering the platelets. The remaining plasma and layer of platelets may then be agitated to re-suspend the platelets in the remaining plasma to obtain a platelet rich plasma.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which:

FIG. 4 is a side view of a plasma centrifuge tube of a platelet rich plasma preparation system the present invention;

FIG. 5 is a top view of a plasma centrifuge tube of a platelet rich plasma preparation system the present invention; and FIG. 6 is a bottom view of a plasma centrifuge tube of a platelet rich plasma preparation system the present invention.

DESCRIPTION OF THE PREFERRED EMBODIMENTS

Figure 1:
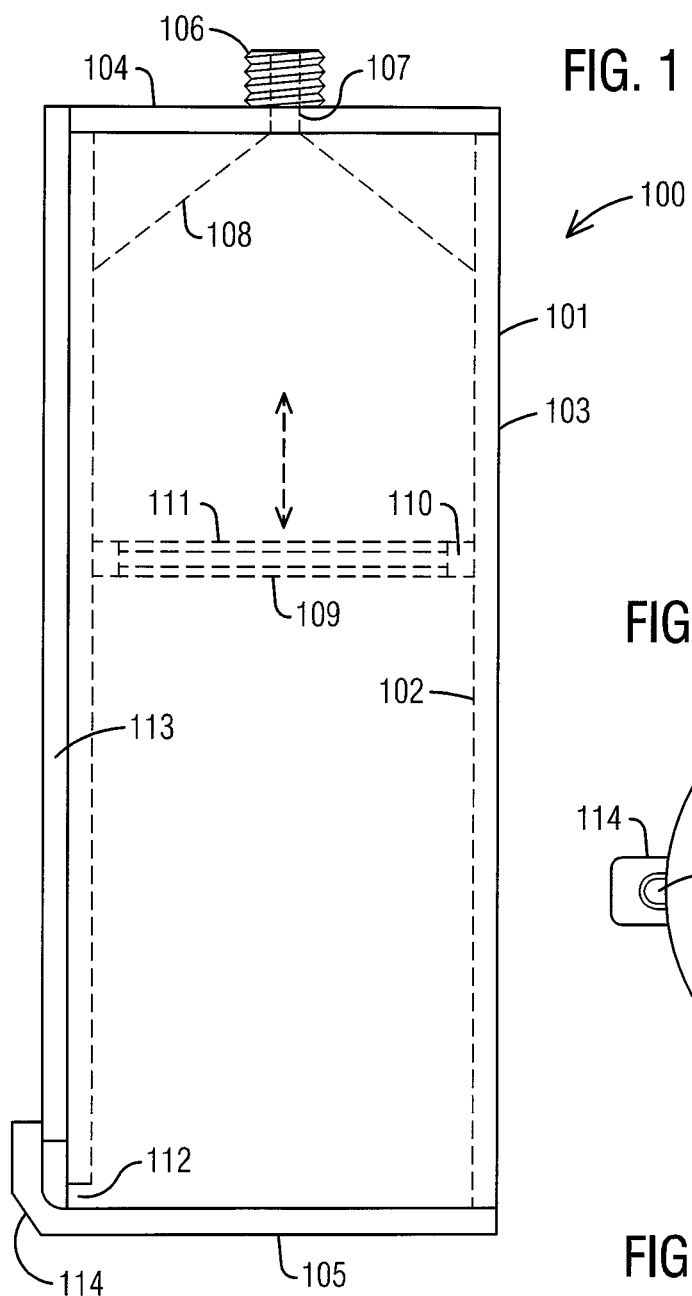
FIG. 1 is a side view of a whole blood centrifuge tube of a platelet rich plasma preparation system the present invention.
Figure 2:
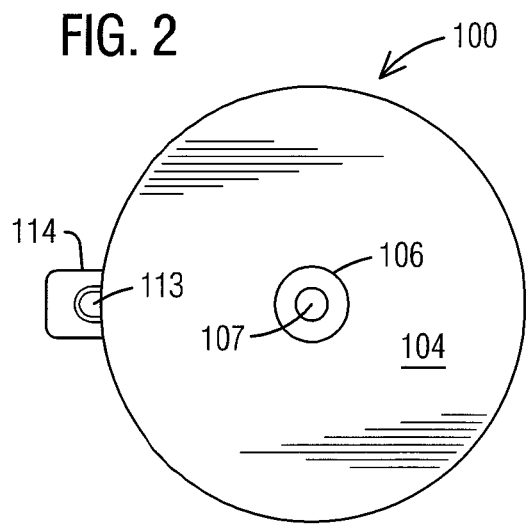
FIG. 2 is a top view of a whole blood centrifuge tube of a platelet rich plasma preparation system the present invention.
Figure 3:
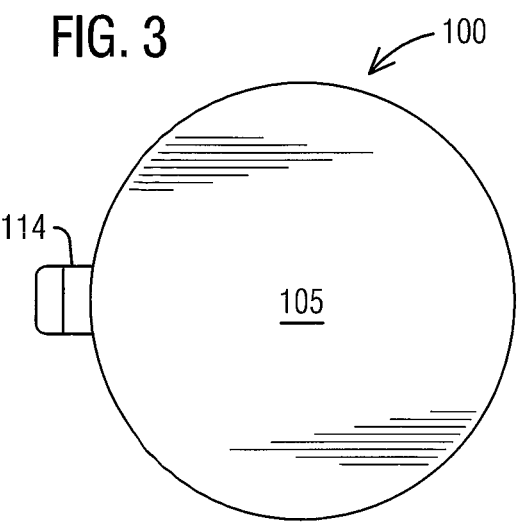
FIG. 3 is a bottom view of a whole blood centrifuge tube of a platelet rich plasma preparation system the present invention.

For purposes of describing the preferred embodiment, the terminology used in reference to the numbered accessories in the drawings is as follows:
- 100. whole blood centrifuge tube, generally
- 101. tubular-shaped side wall
- 102. inner surface
- 103. outer surface
- 104. sealed top end panel
- 105. sealed bottom end panel
- 106. lure lock fitting
- 107. aperture
- 108. conical-shaped inner surface
- 109. piston
- 110. flange
- 111. outer edge of piston
- 112. vent hole
- 113. vent tube
- 114. guard
- 200. plasma centrifuge tube, generally
- 201. tubular-shaped side wall
- 202. inner surface
- 203. outer surface
- 204. sealed top end panel
- 205. sealed bottom end panel
- 206. fill tube
- 207. fill hole
- 208. lure lock fitting
- 209. top end of fill tube
- 210. guard
- 211. bottom end of fill tube
- 212. vent opening With general reference to FIGS. 1-3, a whole blood centrifuge tube 100 of the present invention is illustrated. The whole blood centrifuge tube 100 comprises an inner surface 101, an outer surface 102, a tubular-shaped side wall 103, an outer surface 103, a sealed top end panel 104 and sealed bottom end panel 105. A threaded lure lock fitting 106, or equivalent attachment means, is preferably located centrally on the outer surface 102 of the outer surface of the whole blood centrifuge tube 100 on the top end panel 104 in communication with an aperture 107 located thereon. The inner surface 101 of the whole blood centrifuge tube 100 is angled from an outer perimeter of the aperture 107 downward a predetermined distance toward the tubular-shaped side wall 103, thereby creating a conical-shaped interior surface 108 below the top end panel 104. A piston 109, which is preferably a circular-shaped disk, is located within the whole blood centrifuge tube 100 in a perpendicular position in relation to the tubular-shaped side wall 103 and located below the conical-shaped interior surface 108 below the top end panel 104. A flange 110 is preferably located on an outer edge 111 of the piston 109 to create a fluid tight seal between the piston 109 and the tubular-shaped side wall 103 to prevent fluid from passing by.

A vent hole 112 is located proximate to the bottom end panel 105 to allow communication from the interior of the whole blood centrifuge tube 100 to a vent tube 113. The vent tube 113 is preferably located on the outer surface 102 of the whole blood centrifuge tube 100 and extends from the vent hole 112 to the top end panel 105. The vent tube 113 is preferably fixedly attached to the outer surface 102 of the whole blood centrifuge tube 100 and/or integrated into the tubular-shaped side wall 103. A guard 114 is preferably located proximate to the vent hole 112 and vent tube 113 to protect both from damage and to provide a guide for inserting the whole blood centrifuge tube 100 into a centrifuge bucket.

With general reference to FIGS. 4-6, a plasma centrifuge tube 200 of the present invention is illustrated. The plasma centrifuge tube 200 comprises an inner surface 201, an outer surface 202, a tubular-shaped side wall 203, an outer surface 203, a sealed top end panel 204 and sealed bottom end panel 205. A fill tube 206 is preferably located on the outer surface 202 of the plasma centrifuge tube 200 and extends from a fill hole 207 to the top end panel 204. The fill hole 207 is located on the tubular-shaped side wall 203 and preferably spaced a predetermined distance from the bottom end panel 205 to allow retention of an amount of plasma in the bottom of plasma centrifuge tube 200. A threaded lure lock fitting 208, or equivalent attachment means, is preferably located a top end 209 of the fill tube 206. The fill tube 206 is preferably fixedly attached to the outer surface 202 of the whole blood centrifuge tube 200 and/or integrated into the tubular-shaped side wall 203.

A guard 210 is preferably located on a bottom end 211 of the fill tube 206 to protect the fill tube 206 from damage and to provide a guide for inserting the plasma centrifuge tube 200 into a centrifuge bucket. A vent opening 212 is preferably located on the top end panel 204 to allow pressure within the plasma centrifuge tube 200 to be equalized as plasma is injected into and aspirated out of the plasma centrifuge tube 200.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Having thus described my invention, I claim:

1. A platelet rich plasma preparation system comprising:
   a whole blood centrifuge tube having an inner surface, an outer surface, a tubular-shaped side wall, a sealed top end panel and a sealed bottom end panel;
   an aperture located on the top end panel of the whole blood centrifuge tube;
   a portion of the inner surface of the whole blood centrifuge tube is angled from an outer perimeter of the aperture downward a predetermined distance at an angle toward the tubular-shaped side wall, thereby creating a conical-shaped interior surface below the top end panel;
   a piston located within the whole blood centrifuge tube in a perpendicular position in relation to the tubular-shaped side wall of the whole blood centrifuge tube and below the conical-shaped interior surface below the top end panel of the whole blood centrifuge tube;
   a vent hole is located proximate to the bottom end panel of the whole blood centrifuge tube;

a rigid vent tube connected to the vent hole of the whole blood centrifuge tube; and said rigid vent tube extending up the side wall from the vent hole of the whole blood centrifuge tube and bottom panel to the top end panel of the whole blood centrifuge tube where gas exits said rigid vent tube.

2. The platelet rich plasma preparation system of claim 1 further comprising:

a guard located proximate to the vent hole of the whole blood centrifuge tube to protect the vent hole of the whole blood centrifuge tube from damage.

3. The platelet rich plasma preparation system of claim 1 further comprising:

a threaded lure lock fitting located on the top end panel of the whole blood centrifuge tube in communication with the aperture located thereon.

4. The platelet rich plasma preparation system of claim 1 further comprising:

a flange is located on an outer edge of the piston.

5. The platelet rich plasma preparation system of claim 1 further comprising:

a plasma centrifuge tube having an inner surface, an outer surface, a tubular-shaped side wall having a sealed top end panel and sealed bottom end panel;

a fill tube located on the exterior surface of the plasma centrifuge tube;

a fill hole located on the tubular-shaped side wall of the plasma centrifuge tube; and a vent opening located on the top end panel of the plasma centrifuge tube.

6. The platelet rich plasma preparation system of claim 5 wherein:

said fill hole is spaced a predetermined distance from the bottom end panel of the plasma centrifuge tube to allow retention of an amount of plasma in the bottom of the plasma centrifuge tube.

7. The platelet rich plasma preparation system of claim 5 further comprising:

a threaded lure lock fitting is located on a top end of the fill tube of the plasma centrifuge tube.

8. The platelet rich plasma preparation system of claim 5 further comprising:

a guard is located on a bottom end of the fill tube of the plasma centrifuge tube.

9. A platelet rich plasma preparation device comprising:

a whole blood centrifuge tube having an inner surface, an outer surface, a tubular-shaped side wall, a sealed top end panel and a sealed bottom end panel;

an aperture located on the top end panel of the whole blood centrifuge tube;

a portion of the inner surface of the whole blood centrifuge tube is angled from an outer perimeter of the aperture downward a predetermined distance at an angle toward the tubular-shaped side wall of the whole blood centrifuge tube, thereby creating a conical-shaped interior surface below the top end panel of the whole blood centrifuge tube;

a piston located within the whole blood centrifuge tube in a perpendicular position in relation to the tubular-shaped side wall of the whole blood centrifuge tube and below the conical-shaped interior surface below the top end panel of the whole blood centrifuge tube;

a vent hole is located proximate to the bottom end panel of the whole blood centrifuge tube;

a rigid vent tube connected to the vent hole of the whole blood centrifuge tube; and said rigid vent tube extending up the side wall from the vent hole of the whole blood centrifuge tube and bottom panel to the top end panel of the whole blood centrifuge tube where gas exits said rigid vent tube.

10. The platelet rich plasma preparation device of claim 9 further comprising:

a guard located proximate to the vent hole of the whole blood centrifuge tube to protect the vent hole of the whole blood centrifuge tube from damage.

11. The platelet rich plasma preparation device of claim 9 further comprising:

a threaded lure lock fitting located on the top end panel of the whole blood centrifuge tube in communication with the aperture located thereon.

12. The platelet rich plasma preparation device of claim 9 further comprising:

a flange is located on an outer edge of the piston.

* * * * *